(12) United States Patent
Dawson

(10) Patent No.: US 6,364,529 B1
(45) Date of Patent: Apr. 2, 2002

(54) RADIATION PHANTOM

(75) Inventor: Dana M. Dawson, Cooperstown, NY (US)

(73) Assignee: Med-Tec Iowa, Inc., Orange City, IA (US)

( * ) Notice: Subject to any disclaimer, the term of this patent is extended or adjusted under 35 U.S.C. 154(b) by 0 days.

(21) Appl. No.: 09/693,657

(22) Filed: Oct. 20, 2000

(51) Int. Cl.⁷ ............................................... G01D 18/00
(52) U.S. Cl. ........................................ 378/207; 378/18
(58) Field of Search ........................... 378/207, 18, 204

(56) References Cited

U.S. PATENT DOCUMENTS

| | | | | |
|---|---|---|---|---|
| D250,399 S | | 11/1978 | Helgeson | D10/47 |
| 4,344,183 A | | 8/1982 | Jacobson | 378/207 |
| 4,988,866 A | | 1/1991 | Westerlund | 250/252.1 |
| 5,115,134 A | * | 5/1992 | Slowey | 250/374 |
| 5,162,655 A | | 11/1992 | Peters | 250/498 |
| 5,506,884 A | | 4/1996 | Goodenough et al. | 378/207 |
| 5,544,238 A | * | 8/1996 | Galkin | 378/207 |
| 5,623,139 A | | 4/1997 | Sliski | 250/205 |
| 5,769,779 A | * | 6/1998 | Alderson | 600/1 |
| 5,841,835 A | | 11/1998 | Aufrichtig et al. | 378/207 |
| 5,844,965 A | * | 12/1998 | Galkin | 378/207 |

* cited by examiner

Primary Examiner—Robert H. Kim
Assistant Examiner—Irakli Kiknadze
(74) Attorney, Agent, or Firm—McKee, Voorhees & Sease, P.L.C.

(57) ABSTRACT

The quality assurance phantom for intensity-modulated radiation therapy is adapted for use with multiple dosimetric devices, such as ion chambers, MOSFET's, radiochromatic film, and TLDs. The phantom includes a base to which a static block is fixed. A dynamic block is mounted on the base and is adjustably spaced from the static block. A plurality of film dividers are sandwiched between the blocks. After film is inserted between the film dividers, the blocks are clamped together. The static and dynamic blocks include a plurality of cavities for receiving various dosimeters. The dosimeters are interchangeable within the cavities, so as to enhance the versatility of the phantom.

23 Claims, 2 Drawing Sheets

RADIATION PHANTOM

BACKGROUND OF THE INVENTION

Radiation therapy is a common curative procedure to treat cancer. The goal of the radiotherapy process is to expose the tumor to a sufficient dose of radiation so as to eradicate all cancer cells. The radiation dose is often close to the tolerance level of the normal body tissues. Therefore, it is necessary to determine the dosage levels in different parts of the irradiated body with high accuracy.

Intensity Modulated Radiation Therapy (IMRT) is a complex radiation delivery system, which typically utilizes static ports or dynamic delivery. There are many steps between the calibration of the beam of the therapy radiation unit to the determination of the radiation dose at the desired point of interest in the patient. The alignment of the radiotherapy simulators and treatment machines must be checked regularly to maintain accurate localization and treatment. A comprehensive quality assurance tool is needed in order to verify any series of tests, so that the absolute dose delivered is consistent with the planned dose. In radiation therapy, it is important to ensure that the absolute dose delivered is consistent with the planned dose, and that the critical spatial resolution of that dose is consistent with the planned dose distribution.

The verification of IMRT patient treatment dosages typically is accomplished with custom built or modified dose measurement phantoms. The phantom simulates the body tissue and utilizes dosimeters to measure the radiation dosage before the treatment process on the patient is commenced. Conventional phantoms have limited versatility and do not support multiple dosimetric tools.

Accordingly, a primary objective of the present invention is the provision of an improved phantom for dose verification for intensity modulated radiation therapy.

Another objective of the present invention is the provision of a phantom which supports the commissioning of the entire IMRT system, from imaging through treatment, and which supports verification of the individual treatment plan.

A further objective of the present invention is the provision of an IMRT phantom having versatility in utilizing various dosimeters, including ion chambers, MOSFETs, radiochromatic film, TLD chips, ready pack film, diodes and polymer gel.

Another objective of the present invention is the provision of an improved phantom which provides multiple locations throughout the entire phantom for placement of the dosimeters, so as to enable a clinician to evaluate high dose gradient areas, inhomogeheity regions, and dose distribution at sensitive structures.

Another objective of the present invention is the provision of a quality assurance phantom for radiation therapy having a static block and an adjustable dynamic block, with both blocks being adapted to receive dosimeters.

A further objective of the present invention is the provision of a phantom that selectively utilizes a plurality of film dividers.

A further objective of the present invention is the provision of a phantom having multiple functions, including absolute dose verification in multiple locations throughout the phantom, inhomogeneity correction verification of treatment planning systems, enhanced verification of dose distribution using multiple dosimeters, sensitive structure modules for critical dose distribution evaluation, an effective teaching aid for IMRT, patient plan verification, verification of spatial magnification within CT image, laser calibration tool in a CT suite, three dimensional volumetric verification of dose distribution using multiple dosimeters, comprehensive tool for quality assurance, and commissioning of IMRT treatment planning systems, depth dose verification, and module design for customization and upgrades.

These and other objectives will become apparent from the following description of the invention.

SUMMARY OF THE INVENTION

The phantom of the present invention includes a base with a pair of spaced apart parallel slots. A static block is fixed to the base, and a dynamic block is slidably mounted within the slots such that the space between the static and dynamic blocks is adjustable. One or more film dividers are sandwiched between the static and dynamic blocks. Ready-pack film is inserted adjacent each film divider. The static and dynamic blocks are each adapted to receive a plurality of dosimeters. The blocks and film dividers are oriented vertically upon the base. Clamps secure the static and dynamic blocks together. Preferably, the dosimeters are selected from the group consisting of ion chambers, MOSFETs, radiochromatic film, and TLDS. The selectivity of the film dividers and dosimeters produce a broad range of use in the treatment planning systems, including CT scanners, simulators and linear accelerators.

DETAILED DESCRIPTION OF THE DRAWINGS

Figure 1:
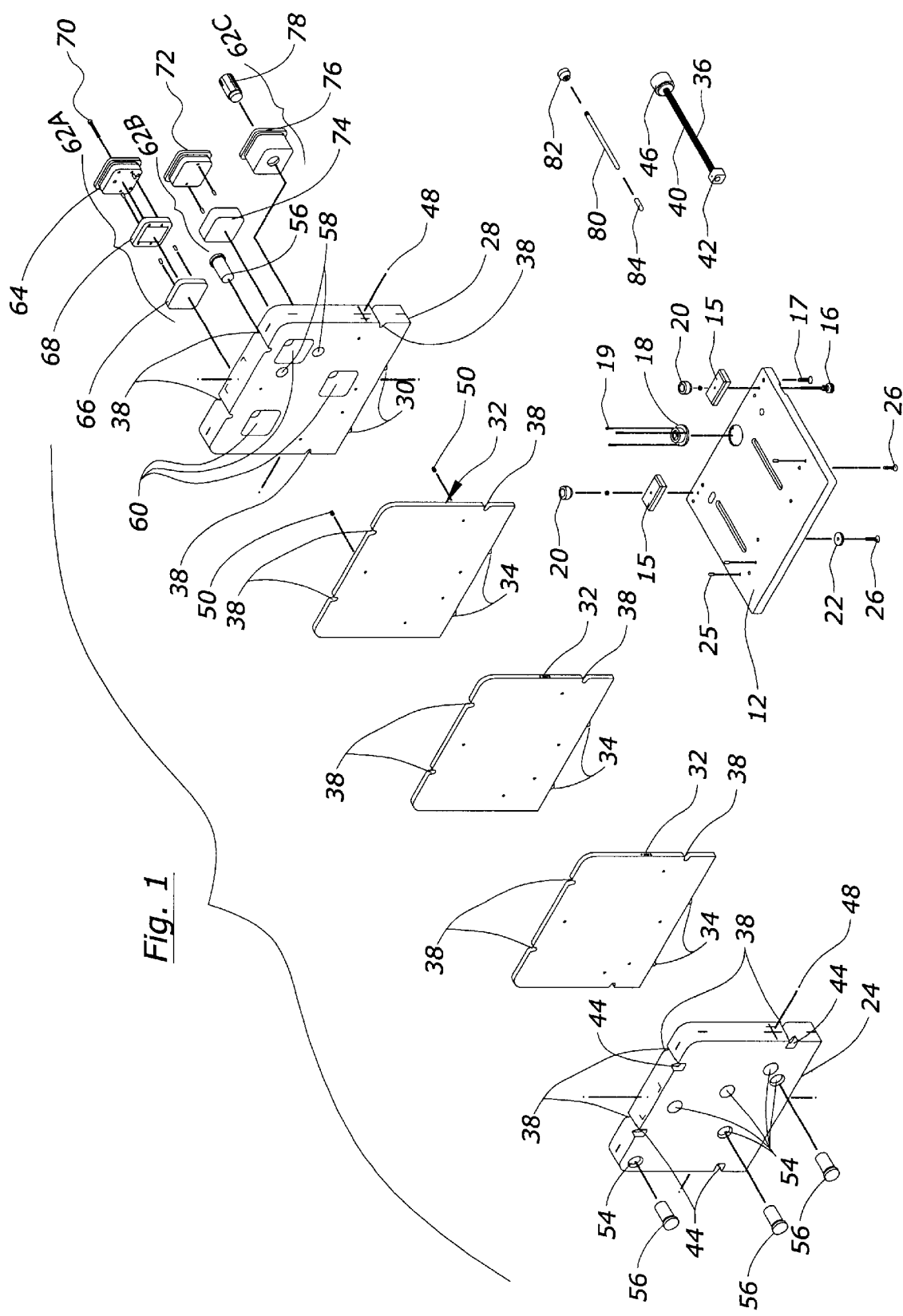
FIG. 1 is an exploded perspective view of the components of the phantom of the present invention.
Figure 2:
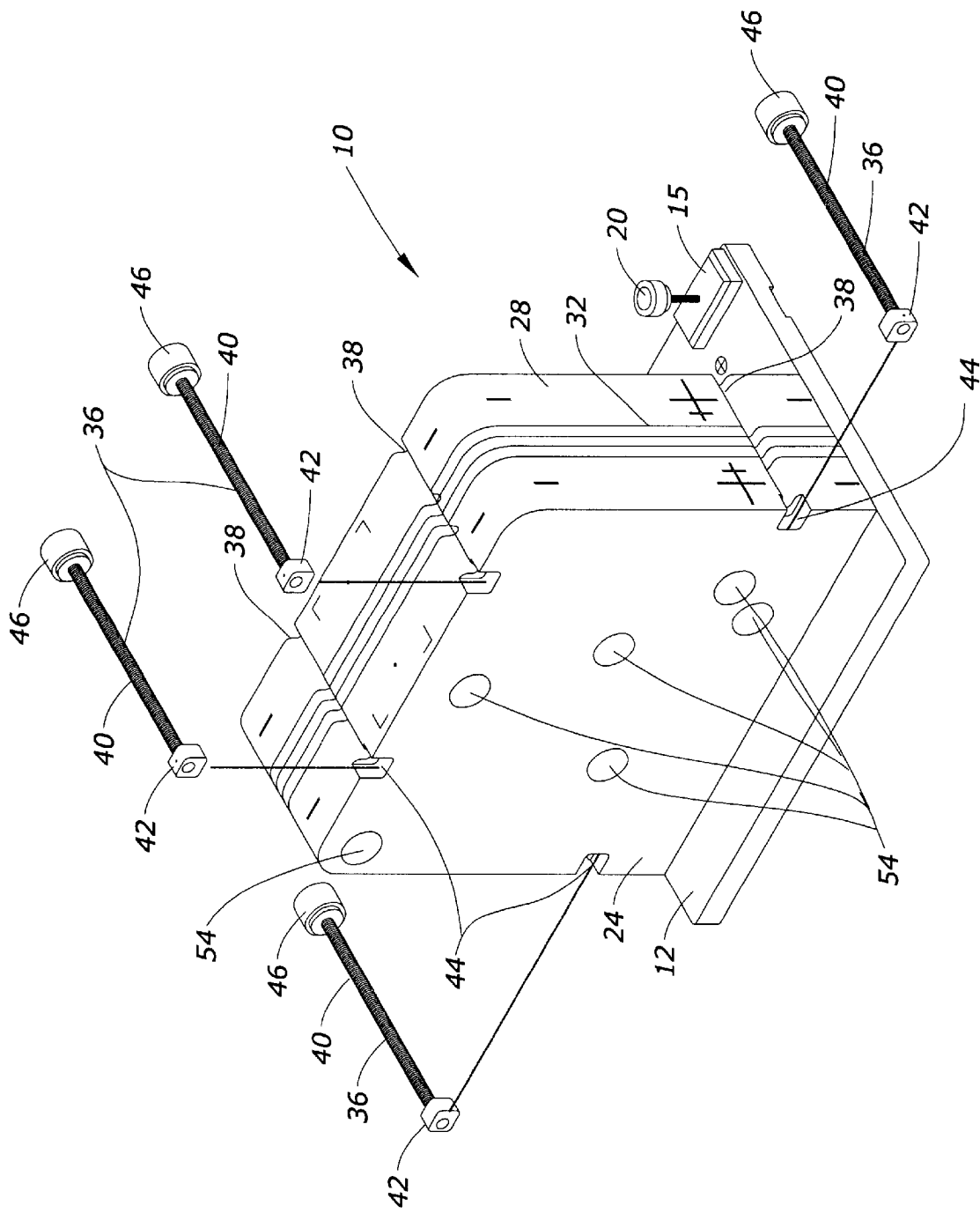
FIG. 2 is a perspective view of an assembled phantom of the present invention, with the clamps exploded out for clarity.

The phantom of the present invention is generally designated in FIG. 2 by the reference numeral 10. The component parts of the phantom are shown in FIG. 1.

The phantom 10 includes a base 12 with a pair of elongated, parallel, spaced apart slots 14 therein. The base 12 includes a pair of threaded feet 16 which can be threadably adjusted in the base 12 so as to level the base. Each adjustable foot 16 extends upwardly through the base and through a stabilizing cap 15, which is attached to the base 12 with screws 17. A bubble level 18 is mounted on the base 12 using screws 19 to assure a level position of the base. The feet 16 are adapted to receive an adjustment knob 20 on top of the base 12 to facilitate extension or retraction of the feet 16. A balancing foot 22 is provided on the base 12 opposite from the adjustable feet 16.

After the phantom 10 is placed on the treatment table, the device can be leveled by turning the knobs 20 of the adjustable feet 16. The phantom 10 can also be indexed to any couch top that is equipped with indexing notches.

A static block 24 is aligned upon the base 12 via pins 25. The pins 25 extend upwardly from the base 12 and are adapted to be received within corresponding holes in the bottom edge of the static block 24. The static block 24 is then fixed to the base using screws 26. The static block has engravings 27 on each side to facilitate calibration of the radiation lasers on an axis.

A dynamic block 28 is mounted on the base 12 via pins 30. The pins 30 extend downwardly from the bottom edge of the dynamic block 28 for receipt in the slots 14 of the base 12. Thus, the dynamic block 28 is slidably mounted on the base 12, such that the spacing between the static block 24 and the dynamic block 28 is adjustable.

One or more film dividers 32 are adapted to be sandwiched between the static block 24 and the dynamic block 28. Each film divider 32 includes a pair of downwardly extending pins 34 which extend into the slots 14 of the base 12 so as to maintain alignment of the film dividers 32 during assembly of the phantom 10.

The static block 24 and dynamic block 28 are secured together with a plurality of bolts or clamps 36, as best seen in FIG. 2. The upper and side edges of the blocks 24, 28 and the film dividers 32 have grooves or recesses 38 formed therein adapted to receive the shank 40 of each bolt 36, thereby providing a substantially unobstructed perimeter edge for the phantom 10. The nut 42 of the bolt 36 is received in a mating recess 44 in the static block 24 so as to prevent turning of the nut. The head 46 of the bolt 36 is adapted to receive a tool to tighten the bolt onto the nut 42. The bolts 36 minimize the air gaps between the blocks 24, 28 and the film dividers 32 by squeezing the assembly together.

The static block 24 and dynamic block 28 each include a plurality of aluminum ball bearings 48 set approximately one centimeter into the blocks, centered on the thickness thereof. The ball bearings 48 serve as fiducial markers. Similarly, each film divider 32 has a plurality of fiducial markers 50, for the x, y and z axes. The markers 50 are located in the same position on each film divider 32 for the x and y axes, but are slightly offset from one another in the z axes. The markers 50 are threaded so that they can be extended or retracted relative to the surface of the film dividers 32, using a screw driver.

The static block 24 has a plurality of cavities 54 adapted to selectively receive ion chamber plugs 56. Similarly, the dynamic block 28 has a plurality of cavities 58 for receiving ion chamber plugs 56. The dynamic block 28 also has a plurality of cavities 60 adapted to receive data packs 62A–62C. The data packs include any type of radiation detector, such as a MOSFET, a TLD chip or radiochromatic film. Also, the detectors in the data packs 62A–62C may have different densities, to simulate different body tissues. For example, the data pack 62A includes a front block 64, a back block 66, a TLD chip 68, and a screw 70 for assembling the front and back blocks 64, 66 and the TLD 68. The data pack 62B includes a back block 72 and a high density lung block 74 to simulate lung tissue. The ion chamber plugs 56 adjacent the data packs 62B are effective to take radiation readings after the beam has passed through the lung block 74. The data pack 62C includes a back block 76 with a circular array bone plug 78 therein. The plug 78 is preferably made of a dense bone-simulating material. The plug 78 has a plurality of slots adapted to receive MOSFET detectors.

The data packs 62A–C are interchangeable in the cavities 60 of the dynamic block 28. Thus, a user can utilize the different radiation detectors of the data packs in any of the cavities 60. The ion chamber plugs 56 are also interchangeable in any of the cavities 54, 56.

A film fiducial marker 80 is provided for the dynamic block 28. The marker 80 includes an outer knob 82 and a vinyl cap 84. The dynamic block 28 includes holes positioned at the same x and y axes locations as on the film dividers, but offset on the z axis.

The base 12, the static and dynamic blocks 24, 28, the film dividers 32 and the ion chamber plugs 56 are preferably made of virtual water material. The front and back blocks 64, 66, 72, and 76 of the data packs 62A–62C are also preferably made of virtual water material. The lung block 74 is preferably made of a high lung material. The bone plug 76 is preferably made of a dense bone material.

In assembling the phantom 10, the static block 24 is mounted on the base 12 using the screws 26 extending upwardly through the base 12. The dynamic block 28 is then positioned on the base 12, and the desired number of film dividers are inserted between the static and dynamic blocks 24, 28. Before the bolts 36 are tightened, ready-pack film is placed between the film dividers 32. The desired ion chamber plugs 56 are inserted into the selected cavities 54, 58 of the blocks 24, 28. The data packs 62A–62C are selectively inserted into the cavities 60 of the dynamic block 28. If desired, MOSFET's are inserted into the bone plug 78 of the data pack 62C. Also, radiochromatic film and/or TLD chips can be installed in the data pack 62A, if desired.

Before a patient is subjected to radiation therapy, a treatment planning system is generated by the treating physician. The planning system includes the quantity of radiation that will be delivered to the tumor. Before patient treatment, the phantom 10 is placed onto the treatment couch to simulate the patient's body. The objective of the phantom is to ensure that the actual delivery of the radiation is the same as that anticipated in the treatment planning system, via the output from the various detectors, including the ion chamber plugs 56 and the data packs 62A–62C. After being subjected to the prescribed radiation, such as from a CT scanner or simulator, the ion chamber plugs 56 and data packs 62A–62C are removed from the blocks 24, 28 and read by a physicist. The measurements made by the detectors are then compared to the treatment planning system prescription. The detectors of the phantom 10 collect data in three dimensions simultaneously. Also, the data packs 62A–62C can be rotated at 90° intervals, so as to obtain readings at 90°, 180°, 270°, and 360°, thereby building a locus around the data packs.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A phantom for dose verification for intensity-modulated radiation therapy, comprising:
    a base;
    a static block fixed on the base;
    a dynamic block mounted on the base in adjustably spaced relation to the static block;
    at least one film divider positioned on the base between the static and dynamic blocks; and
    a plurality of radiation dose detectors mounted in at least one of the static and dynamic blocks.

2. The phantom of claim 1 wherein the base includes a pair of parallel slots and the dynamic block is slidable within the slots.

3. The phantom of claim 1 wherein the static and dynamic blocks and the film dividers are oriented vertically upon the base.

4. The phantom of claim 1 wherein the detectors are selected from the group consisting of ion chambers, MOSFETs, radiochromatic film, TLD chips, diodes and polymer gels.

5. The phantom of claim 1 wherein the detectors have different densities from one another.

6. The phantom of claim 1 wherein the static and dynamic blocks are secured together with clamps.

7. The phantom of claim 1 wherein the static and dynamic blocks each have cavities for selective insertion of the detectors.

8. The phantom of claim 7 wherein the detectors are rotatable within the cavities.

9. The phantom of claim 7 wherein the detectors are interchangeable in the cavities.

10. A quality assurance phantom for multiple dosimetric devices, comprising:

a pair of blocks spaced from one another and being adapted to receive radio-sensitive film therebetween, the blocks each having a plurality of cavities therein; and a plurality of dosimeters interchangeably mountable in the cavities of the blocks for measuring radiation dosages.

11. The phantom of claim 10 further comprising a plurality of film dividers, sandwiched between the blocks.

12. The phantom of claim 10 wherein the blocks are mounted on a base.

13. The phantom of claim 10 wherein the blocks are adjustably spaced from one another.

14. The phantom of claim 10 wherein the dosimeters include an ion chamber plug.

15. The phantom of claim 10 wherein the dosimeters include a MOSFET.

16. The phantom of claim 10 wherein the dosimeters include radiochromatic film.

17. The phantom of claim 10 wherein the dosimeters include a TLD.

18. The phantom of claim 10 wherein the dosimeters include ready pack film.

19. The phantom of claim 10 wherein the dosimeters include diodes.

20. The phantom of claim 10 wherein the dosimeters include polymer gel.

21. The phantom of claim 10 wherein the dosimeters have different densities from one another.

22. The phantom of claim 10 wherein the dosimeters are rotatable in the cavities.

23. The phantom of claim 10 wherein the blocks are vertically oriented.

* * * * *

//
(12) EX PARTE REEXAMINATION CERTIFICATE (5016th)
United States Patent
Dawson

(10) Number: US 6,364,529 C1
(45) Certificate Issued: Nov. 9, 2004

(54) RADIATION PHANTOM

(75) Inventor: Dana M. Dawson, Cooperstown, NY (US)

(73) Assignee: Med-Tec Iowa, Inc., Orange City, IA (US)

Reexamination Request:
No. 90/006,311, Jun. 19, 2002

Reexamination Certificate for:
| | |
|---|---|
| Patent No.: | 6,364,529 |
| Issued: | Apr. 2, 2002 |
| Appl. No.: | 09/693,657 |
| Filed: | Oct. 20, 2000 |

(51) Int. Cl.$^7$ .............................................. G01D 18/00
(52) U.S. Cl. ........................................ 378/207; 378/18
(58) Field of Search ........................... 378/18, 204, 207

(56) References Cited

PUBLICATIONS

Phantoms for IMRT Dose Distribution—by D.Low et al, 1998, J.Rad Oncology—vol. 40, pp. 1231–1235.
Quality Assurance of Serial Tomotherapy—D.Low et al, 1998, J.Rad Oncology vol. 421, pp. 681–692.
PTW Application note # D378,208,0/0 of Sep. 2000.
ICRU report #48 of Jun. 15, 1992.
A Filtration Method for Improving Film Dosimitry—by J. Yeo et al, Medphys 24, Dec. 1997, pp. 1943–1953.
A Method for determining multileaf collimator transmission—by J.Arnfield et al, Medphys 27, Oct. 2000, pp. 2231–2241.

CIRS "Plastic Water"™ from 1998 CIRS catalog/ 1992 Trademark.
ATOM catalog excerpt 1993.
Dosimetric Verification of Intensity Modulated Beams by X. Wang et al , Medphys 23 ,Mar. 1996, pp. 319.
Evaluation of polymer gels and MRI as a 3D Dosimeter—by D.Low et al, Medphys 26, Aug. 99 , pp. 1542–1551.
AAPM presentation,"A system for comprehensive 3D verification of IMRT treatment delivery "—by G.Gluckman , Jul. 29, 1999.
RMI catalog 1987, excerpt describing Phantom/Vice combination.
Rando Phantom, medical applications, Lanzl,1973.
PTW Application note D168.208.0/2 keyed to published references 1997 and 1999.
AAPM Annual Meeting, 1999, Poster PO–T–65.
NOMOS data sheet , copyright 1999, on Peacock system.

*Primary Examiner*—Craig E Church

(57) ABSTRACT

The quality assurance phantom for intensity-modulated radiation therapy is adapted for use with multiple dosimetric devices, such as ion chambers, MOSFET's, radiochromatic film, and TLDs. The phantom includes a base to which a static block is fixed. A dynamic block is mounted on the base and is adjustably spaced from the static block. A plurality of film dividers are sandwiched between the blocks. After film is inserted between the film dividers, the blocks are clamped together. The static and dynamic blocks include a plurality of cavities for receiving various dosimeters. The dosimeters are interchangeable within the cavities, so as to enhance the versatility of the phantom.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–23 is confirmed.

\* \* \* \* \*